United States Patent [19]

Fukada et al.

[11] Patent Number: 5,003,824
[45] Date of Patent: Apr. 2, 1991

[54] VIBRATION/ACCELERATION SENSOR

[75] Inventors: Tetsuji Fukada; Masayuki Wakamiya, both of Suita; Kikuo Kainou, Hirakata, all of Japan

[73] Assignee: Matsushita Electric Industrial Co., Ltd., Osaka, Japan

[21] Appl. No.: 456,372

[22] Filed: Dec. 26, 1989

[51] Int. Cl.⁵ .............................................. G01D 21/00
[52] U.S. Cl. .................................. 73/651; 73/517 R; 73/DIG. 4; 310/331
[58] Field of Search ............ 73/651, 652, 654, 517 R, 73/DIG. 1, DIG. 4; 310/329, 331

[56] References Cited

U.S. PATENT DOCUMENTS 3,167,668  1/1965  Nesh .
4,364,259  12/1982  Muranaka et al. .................. 73/654
4,713,573  12/1987  Gansert et al. .................... 310/329

FOREIGN PATENT DOCUMENTS 0100501  2/1984  European Pat. Off. .
5970923  4/1959  Japan .
1148969  6/1989  Japan .................................. 73/654
1148970  6/1989  Japan .

*Primary Examiner*—Hezron E. Williams
*Assistant Examiner*—Rose Finley
*Attorney, Agent, or Firm*—Stevens, Davis, Miller & Mosher

[57] ABSTRACT

A vibration/acceleration sensor is provided which includes a basic sensor unit fixed to a casing adapted to be mounted on a body the vibrations of which are to be detected. The sensor unit is surrounded by a resinous material having a low heat transfer coefficient. The sensor unit includes a vibration detecting unit including a piezoelectric bending vibrator, thin plates each formed of, for example, a resinous material having a low heat transfer coefficient, provided respectively on the upper and lower surfaces of the vibration detecting unit, and a signal processing circuit formed on the upper thin plate.

4 Claims, 3 Drawing Sheets

F I G. 1
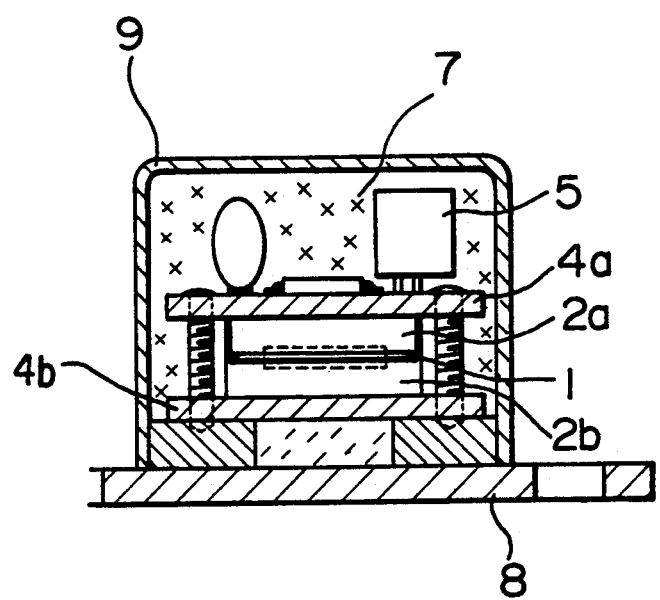

VIBRATION/ACCELERATION SENSOR

BACKGROUND OF THE INVENTION

1. Field of the Invention

The present invention relates to a vibration/ acceleration sensor for detecting the vibration of a substance and the acceleration caused due to such vibration by utilizing the electromechanical conversion characteristics of a piezoelectric material.

2. Statement of the Related Art

In general, conventional piezoelectric type vibration-/acceleration sensors for detecting the elastic vibration of a vibrating body include those of a longitudinally effective type which utilize compression and tension in the thicknesswise direction of a piezoelectric element and those of a shear-effect type which utilize a shear force in the piezoelectric element. However, in the case where the resonance frequency is made to coincide with a specific vibration of a vibrating substance to detect only specified frequency components, or in the case where the vibration components in a specified region of frequencies are detected so as to increase the sensitivity in the region of low frequencies, a laterally effective type vibrator, i.e., a cantilever type vibrator utilizing a bending vibration mode has hitherto been widely employed. In case of the vibration/acceleration sensor having the cantilever type vibrator structure, a difficulty is encountered in satisfying conditions for fixing one end of the vibrator. In order to solve this problem, one conventional technique such as that disclosed in Japanese Patent Unexamined Publication No. 59-70923 stabilizes the fixing of one end of the vibrator with the use of a cantilever type bending vibrator constituting a vibration detecting portion which is fabricated by (1) forming a slit in a laminated plate-like member, such as a disc-like piezoelectric element, with the bending vibrator being integral, at one end, with the laminated plate-like piezoelectric element, and by (2) fixing the outer surface of the bending vibrator in place and supporting the same, thus making it possible to stabilize the fixing condition of the vibrator.

The above-described prior art piezoelectric vibration/acceleration sensor detects a mechanical force such as acceleration and, at the same time, generates an electrical charge in accordance with variations in the ambient temperature. This is due to the pyroelectric effect of a piezoelectric material and the electrical charge generation is given by the following formula:

$$dQ/dt = k \, dT/dt \quad (1)$$

where Q represents the electrical charge, T the temperature, t the time, and k a proportional constant. Namely, the generation of this electrical charge can not be distinguished from the electrical charge produced due to an acceleration desired to be detected, causing a large error in detecting the degree of acceleration. The acceleration sensor of a structure wherein two sheets of piezoelectric materials are bonded together can theoretically achieve mutual cancellation of their generated charges in both types, that is, (1) a serial type in which the two sheets of piezoelectric material are bonded together so that the directions of the polarizing axes may become opposite to each other and so that the respective opposing surfaces of the two bonded sheets may serve as signal take-out electrodes, and (2) a parallel type in which the respective opposing surfaces of the two upper/lower bonded sheets are connected together to serve as a signal take-out electrode and the bonded surface electrode is also used as a signal take-out electrode. However, in the conventional acceleration sensor, transfer of heat to the piezoelectric material is non-uniform and in addition the electrical charges generated due to the pyroelectric effect fail to cancel each other out under severe temperature conditions so that output signals are generated from an asymmetrical electrode constituted by a bending vibration mode vibrator serving as the signal take-out portion. This makes it impossible to provide an acceleration sensor capable of achieving highly precise detection.

SUMMARY OF THE INVENTION

An object of the present invention is to provide a high-precision vibration/acceleration sensor which reduces the level of the output signals generated due to variations in the ambient temperature.

To attain the above object, the present invention provides a vibration/acceleration sensor which comprises a basic sensor unit including a vibration detecting unit having a piezoelectric bending vibrator, upper and lower thin plates attached respectively on the upper and lower surfaces of the vibration detecting unit, and a signal processing circuit formed on the upper thin plate, a casing adapted to be attached to a body whose vibrations are to be detected and secured thereon with the basic sensor unit, and a resinous material enclosing the basic sensor unit.

In the vibration detecting unit in which metal fixing members are fixed to the bending vibration mode vibrator on both upper and lower surfaces thereof, the ambient heat is substantially uniformly transferred to the vibrator by way of the fixing members. Therefore, the temperature gradient, which varies depending upon positions, becomes moderate. In addition, the thin plates such as those composed of resinous materials having low heat transfer coefficients are provided, respectively, on the top and bottom surfaces of the vibration detecting unit, and the resulting unit is enclosed by resinous materials. Therefore, transfer of heat up to the vibration detecting unit is retarded, resulting in minimizing the undesirable effects upon the sensor output.

BRIEF DESCRIPTION OF THE DRAWINGS

FIG. 1 is a sectional view showing a vibration acceleration sensor according to one embodiment of the present invention;

DESCRIPTION OF THE PREFERRED EMBODIMENT

A vibration/acceleration sensor according to an embodiment of the present invention will now be described in detail with reference to the drawings.

Figure 2:
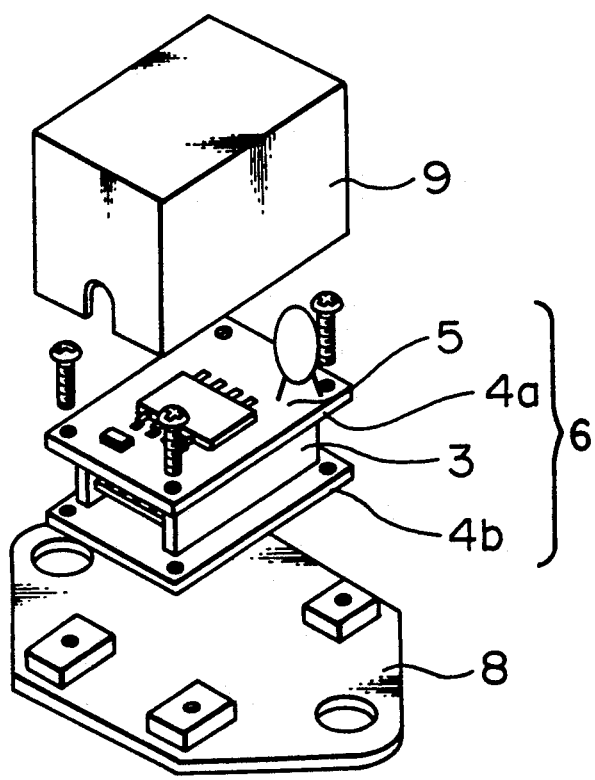
FIG. 2 is an exploded perspective view thereof.
Figure 3:
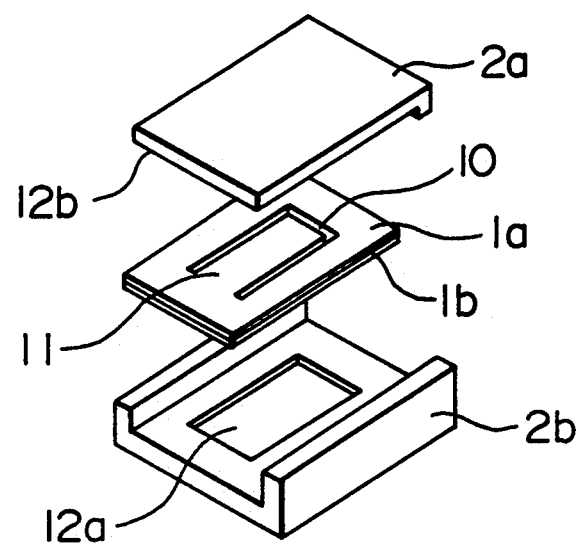
FIG. 3 is an exploded perspective view showing the vibration detecting unit.

FIG. 1 is a sectional view showing a vibration/ acceleration sensor in accordance with an embodiment of the present invention, and FIG. 2 is an exploded perspective view showing the vibration detecting unit. FIG. 3 is an exploded perspective view illustrating the vibration detecting unit. A piezoelectric bond element 1 is prepared which has a structure in which plate-like piezoelectric components 1a, 1b having polarizing axes in the thicknesswise direction and formed with symmetrical electrodes, respectively, on their opposing surfaces are bonded together. A "U"-shaped slit 10 is formed in the piezoelectric bond element 1 by, for example, a laser beam machining. Thus, the portion which is enclosed by the slit 10 constitutes a bending vibration mode vibrator 11 having a cantilever type structure. In the case where the bending vibration mode vibrator 11 is of a serial type in which the plate-like piezoelectric members 1a, 1b are bonded together in such a manner that the directions of their polarizing axes are opposite to each other, the upper and lower surface electrodes thereof function as output take-out electrodes. In the case where the bending vibration mode vibrator 11 is of a parallel type in which the plate-like piezoelectric members 1a, 1b are bonded together with their polarizing axes being directed in the same direction, the upper and lower surface electrodes thereof are connected together and these electrodes and the bonded surface electrodes are used as output signal take-out electrodes. The vibration detecting unit 3 is one which has been prepared by clamping the piezoelectric element 1 constituting the bending vibrator between fixing members 2a, 2b which are respectively formed, as shown in FIG. 3, with a groove 12a, adjacent a displacing section of the bending vibrator 11, and a cut-out region 12b adjacent the outer periphery of the bending vibrator 11 in order to secure the fixing members 2a, 2b. Members 2a, 2b are made of copper having a high heat transfer coefficient (approximately 400 W/mk), and are secured together by an epoxy-based adhesive agent. By making the vibration detecting unit 3 into such a structure as mentioned above, the ambient heat is transferred to the bending vibrator 11 via the fixing members, so that transfer of heat to the bending vibrator 11 constituting the acceleration detecting portion is substantially uniformly effected from the surrounding fixing portions, thus reducing the temperature gradient which varies depending upon positions. In addition, resinous thin plates 4a, 4b, such as printed circuit boards, that is glass epoxy based print boards on which there is formed a signal processing circuit 5 including an impedance conversion circuit and a filter amplifier circuit, are mounted, respectively, on the top and bottom surfaces of the vibration detecting unit 3, thereby forming a basic sensor unit 6. The basic sensor unit 6 is fixed onto a casing 8 formed of, for example, metal onto a body whose vibration is to be detected. While variations in heat from the vibration detection body are transmitted by way of the casing 8, a time lag occurs until the heat is transferred up to the vibration detecting unit 3, on account of transfer of heat thereto via the print board having a low heat transfer coefficient. In consequence, signal components due to the pyroelectric effect come to have lower frequencies, and the degree of variations, with time, in temperature shown in the above-mentioned formula (1) becomes lower. This causes suppression of the signal. Thus, the undesirable effects upon the sensor signals can be reduced. Such undesirable effects can be further reduced by charging urethane resin 7 into a space between the sensor cover 9 and the basic sensor unit 6. In this way, the output signals which are produced due to the variations in temperature are suppressed, thereby enabling a highly precise detection of the acceleration.

Figure 4:
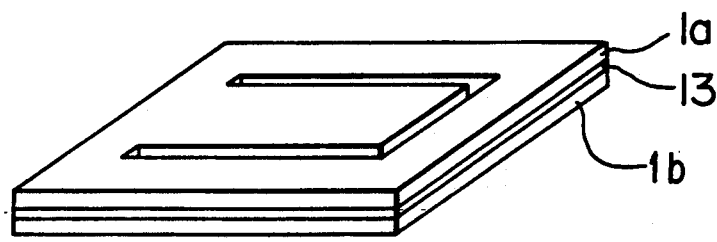
FIG. 4 is a perspective view showing another embodiment of the present invention.

FIG. 4 is a perspective view of a piezoelectric element portion in accordance with another embodiment of the present invention. By using a piezoelectric bond element 1 of a structure wherein plate-like piezoelectric members 1a, 1b are bonded together with intervention, therebetween, of a metallic thin plate 13 made of materials such as cobal, 42% Ni-Fe and the like, having a thermal expansion coefficient equal to, or approximately equal to, that of the piezoelectric material, it is possible to increase the mechanical strength against impact such as that occurring at the time of, for example, a fall-down. If the piezoelectric element of FIG. 4 is substituted for that of the first embodiment and if depth of a space defined by the recesses 12a, 12b formed in the fixing members 2a, 2b (shown in FIG. 3) is made equal to a displacement of the bending vibrator 11 upon permissible acceleration, the bending vibrator can be prevented from being displaced in response to an input greater than the permissible acceleration. This leads to protecting the bending vibrator 11. Thus, the bending vibrator comes to have a higher mechanical strength against impact at the time of, for example, a fall-down.

According to the present invention, since the vibration detecting unit permits substantially uniform transfer of the surrounding heat to the vibrator by way of the fixing members, variations in temperature gradient depending upon positions is reduced. Further, the thin plates, each made of a low-heat-transfercoefficient resinous material or the like, are attached, respectively, to the upper and lower surfaces of the vibration detecting unit and, in addition, such thin plates are covered by resinous material. Thus, a time lag is effected until heat reaches the vibration detecting unit. Thus, the undesirable effects upon the sensor output can be reduced.

What is claimed is:

1. A vibration/acceleration sensor comprising:
 a basic sensor unit including a vibration detecting unit containing therein a piezoelectric bending vibrator having upper and lower surfaces, a first thin plate and a second thin plate provided respectively on the upper and lower surfaces of said vibration detecting unit,
 a signal processing circuit provided on at least one of said first thin plate and said second thin plate,
 a casing means for being mounted onto a body whose vibrations are to be detected, and a resinous material enclosing said basic sensor unit;
 and wherein each of said first thin plate and said second thin plate is formed of a resinous material having a low heat transfer coefficient and include a printed circuit board formed of glass epoxy resin.

2. A vibration/acceleration sensor as claimed in claim 1, wherein said vibration detecting unit further comprises a piezoelectric element composed of two plate-like piezoelectric components bonded together to provide upper and lower surfaces, said two plate-like piezoelectric components having a polarizing axis in a thicknesswise direction thereof and having electrodes on said upper and lower surfaces thereof, a bending vibration mode vibrator comprising a member provided by forming a slit in said piezoelectric element, and fixing members having a high heat conductivity for fixing said bending vibration mode vibrator to clamp the same therebetween.

3. A vibration/acceleration sensor as claimed in claim 2, wherein said two plate-like piezoelectric components are bonded together with a metallic thin plate interposed therebetween, said metallic thin plate having a thermal expansion coefficient which is approximately equal to that of said piezoelectric element.

4. A vibration/acceleration sensor as claimed in claim 2, wherein said fixing members include displacing portions formed, respectively, with grooves having a depth which is equal to a displacement of said bending vibration mode vibrator at the time of a maximum permissible acceleration.

* * * * *